United States Patent [19]
Meijer

[11] Patent Number: 5,360,594
[45] Date of Patent: Nov. 1, 1994

[54] CONTROL SYSTEM FOR MEDICAL WASTE DISPOSAL UNIT

[75] Inventor: Robert S. Meijer, San Diego, Calif.

[73] Assignee: Winfield Industries, San Diego, Calif.

[21] Appl. No.: 153,267

[22] Filed: Nov. 15, 1993

Related U.S. Application Data

[63] Continuation of Ser. No. 941,409, Sep. 8, 1992, abandoned, which is a continuation-in-part of Ser. No. 690,116, Apr. 23, 1991, which is a continuation-in-part of Ser. No. 511,275, Apr. 19, 1990, Pat. No. 5,089,228.

[51] Int. Cl.$^5$ .............................................. A61L 2/16
[52] U.S. Cl. ........................................ 422/37; 422/32; 422/108; 422/109; 422/111; 422/292; 423/DIG. 18; 241/DIG. 38
[58] Field of Search ............. 422/28, 32, 37, 108, 422/109, 111, 292; 423/DIG. 18; 241/DIG. 38

[56] References Cited

U.S. PATENT DOCUMENTS

| | | | |
|---|---|---|---|
| 4,294,804 | 10/1981 | Baran | 422/28 |
| 4,576,792 | 3/1986 | Martensson | 422/109 |
| 4,710,350 | 12/1987 | Petersen | 422/109 |
| 4,822,513 | 4/1989 | Corby | 252/106 |
| 4,908,188 | 3/1990 | Jefferis, III et al. | 422/28 |
| 4,923,677 | 5/1990 | Simon et al. | 422/37 |
| 4,971,761 | 11/1990 | Johnson | 422/109 |
| 5,078,965 | 1/1992 | Pearson | 422/28 |
| 5,089,228 | 2/1992 | Meijer | 422/37 |
| 5,122,344 | 6/1992 | Schmoegner | 422/28 |

OTHER PUBLICATIONS

Medical Safe TEC, The ultimate in total destruction and decontamination of infectious waste.
Mediclean Technology, Inc., Infectious Waste Processor Model IWP-1000.

*Primary Examiner*—Timothy M. McMahon
*Attorney, Agent, or Firm*—Nydegger & Associates

[57] ABSTRACT

A control system for regulating the decontamination of waste in a reaction chamber is provided. The control system monitors the chamber temperature and disinfectant concentration. Using the disinfectant concentration, the control system then calculates the minimum temperature required to maintain a specified level of decontamination. This minimum temperature is then compared to the actual temperature by the control system. If the actual temperature is below the minimum, the control system operates a heater to heat the reaction chamber. Additional temperature control can also be provided by the control system. If desired, the control system compares the actual chamber temperature to an ideal operating temperature. If the actual temperature exceeds the ideal temperature, the system cools the chamber by pumping in additional low temperature disinfectant. In this manner, the additional disinfectant maintains the level of decontamination as the chamber temperature decreases.

26 Claims, 4 Drawing Sheets

CONTROL SYSTEM FOR MEDICAL WASTE DISPOSAL UNIT

"This is a continuation-in-part of co-pending application Ser. No. 07/941,409, filed Sep. 8, 1992 now abandoned which is a continuation-in-part application of application Ser. No. 07/690,116, filed Apr. 23, 1991 which is a continuation-in-part of application Ser. No. 07/511,275, filed on Apr. 19, 1990 and which issued as U.S. Pat. No. 5,089,228.

TECHNICAL FIELD

The present invention relates generally to treatment of infectious waste. More particularly, the present invention relates to a control system for devices which mechanically fragment and decontaminate infectious waste. The present invention is particularly, though not exclusively, useful for monitoring and regulating the temperature and the disinfectant concentration during decontamination of infectious waste.

BACKGROUND OF THE INVENTION

The disposal of infectious waste from hospitals and other medical establishments is a major problem. Indeed, the importance of proper and effective infectious waste disposal has become of greater concern in recent years, due to an increased awareness of health problems such as the AIDS epidemic. In part because of the AIDS epidemic, definitions of what constitutes "infectious waste" are being broadened. Consequently, the volume of infectious waste which must be disposed of is increasing. Accordingly, the need for a system or apparatus which will accomplish the safe, efficacious, and cost effective treatment of significant volumes of infectious waste for disposal is growing.

One method for decontaminating infectious waste involves incineration, wherein the waste is burned and the decontaminated ashes are properly disposed. An alternative treatment method is to disinfect the waste in a steam autoclave prior to waste disposal. While effective for their intended purposes, both incinerators and autoclaves present ancillary problems. Incinerators, for example, are difficult and costly to construct and are relatively expensive to maintain in an environmentally safe manner. Autoclaves too, present additional problems, such as odor, cost and operational complexity. Additionally, waste which has been disinfected by autoclaving typically requires further treatment procedures, such as incineration or shredding, prior to final disposition of the waste in such places as landfills.

With the above discussion in mind, alternative infectious waste treatment systems have been proposed to disinfect the waste in preparation for disposal. According to these proposals, a solid infectious waste is contacted with a disinfectant solution containing a chlorine compound to decontaminate the waste. The decontaminated waste may then be disposed in ordinary landfills.

Unfortunately, decontamination of waste using chlorine compounds presents certain technical complications. First, liquid disinfectant loses its disinfectant potency during prolonged storage. Thus, there is a need to use liquid disinfectant that is relatively "fresh" in order to achieve an acceptable degree of waste decontamination. Second, it is relatively difficult to ensure that an appropriate concentration of the disinfectant has contacted the waste during the treatment process. It is also important, however, to avoid applying too high a concentration of chlorine compound to the waste in order to avoid undesirable results, such as corrosive effects and the release of toxic gasses. The present invention recognizes that precise amounts of disinfectant precursors can be stored for relatively lengthy time periods without losing their potency and can be mixed with water to form a chlorinated disinfectant solution when needed. The resulting solution can be used to decontaminate infectious waste in a system that mechanically shreds the waste.

Accordingly, it is an object of the present invention to provide a control system for waste treatment which ensures precise amounts of a chlorine-based disinfectant are blended with infectious waste to decontaminate the waste. Another object of the present invention is to provide a control system for waste treatment which closely regulates the temperature of the infectious waste while it is being disinfected. Yet another object of the present invention is to provide a control system that balances the addition of heat and disinfectant during the decontamination process to render the waste substantially noninfectious. Finally, it is an object of the present invention to provide a control system for waste treatment which is relatively easy and comparatively cost-effective to implement.

SUMMARY OF THE INVENTION

The present invention is a control system for treating infectious waste in a multi-stage treatment device. More particularly, the device and method of present invention relate to process control of the disinfecting or decontaminating stage of the multi-stage treatment device.

In operation, the waste is shredded, granulated and mixed with an initial quantity of disinfectant prior to being decontaminated in a reaction chamber. In order to ensure satisfactory decontamination of the waste, a control system maintains the treatment fluid at the required conditions for a specified rate of biological kill. The present invention recognizes that the desired level of decontamination can vary and therefore allows the operator to specify the level of decontamination desired in terms of a rate of kill.

The control system used can be either a single loop or a cascade control system. The single loop system regulates disinfectant fluid temperature as a function of the rate of kill and the actual disinfectant concentration while the cascade system regulates temperature and disinfectant concentration as a function of the target kill rate and the desired temperature.

The primary component of the single loop control system is a control unit including a microprocessor. This control unit is connected to an electronic thermometer and a gas analyzer. The thermometer includes a temperature probe located inside the reaction chamber and is able to provide the actual fluid temperature to the control unit.

The gas analyzer connected to the control unit analyzes gas samples received from the reaction chamber. Air is provided to the gas analyzer by an air pump connected to the reaction chamber. This air pump "bubbler" strips gas from the reaction chamber and passes it to the gas analyzer. The sample is analyzed by the gas analyzer to determine the concentration of disinfectant present and the results are then provided to the control unit.

Knowing the desired rate of kill, the control system is able to calculate a target or set point temperature for any given disinfectant concentration as measured by the gas analyzer. Having calculated the set point temperature required, the control system performs a comparison of the actual reaction chamber temperature to the calculated set point temperature.

If the result of the comparison of the actual and set point temperatures indicates the actual temperature of the reaction chamber is below the set point temperature, the control unit activates a heater to heat the reaction chamber. If, on the other hand, the actual temperature is above the set point, the heater turns off to allow the system to cool.

In this manner, the control system maintains the desired rate of kill by regulating the chamber temperature to compensate for changes in the disinfectant concentration.

A cascade loop control system is also provided which maintains the specified rate of kill while keeping the fluid in the reaction chamber at or near a specified temperature. In addition to the components of the single loop system described above, the cascade loop system includes a second feedback control loop to maintain the reaction chamber at or near an ideal operation temperature. To accomplish the additional temperature control, the control unit of the cascade loop system also controls a pump. This pump can transfer additional disinfectant from a disinfectant reservoir to the reaction chamber.

As in the single loop system, the operator for the cascade loop system specifies the desired rate of kill. Additionally, for the second feedback control loop, the control unit requires specification of an ideal operating temperature. This ideal temperature is preferably preset within the control unit, but can alternatively be entered by the operator.

During operation of the cascade loop system, the first control loop operates in substantially the same manner as does the single loop of the single loop system. More specifically, the control unit monitors the actual chamber temperature and disinfectant concentration, and knowing the desired rate of kill, the control unit can calculate a set point temperature. If the actual temperature is below the set point temperature the heater is again operated.

Operation of the second control loop compares the actual temperature to the ideal temperature. If the actual temperature is above the ideal temperature, then the control unit operates the pump to add additional disinfectant to the chamber. Adding disinfectant lowers the chamber set point and consequently the need to add heat. This, combined with the periodic addition of unheated water to the system, lowers the temperature of the fluid in the reaction chamber. Decontamination levels, which are proportional to the fluid temperature and the disinfectant concentration in the reaction chamber, are maintained during chamber cooling by the additional disinfectant.

In this manner, the cascade loop control system maintains the desired rate of kill as well as the ideal operating temperature by regulating both the temperature and the concentration of the disinfectant in the reaction chamber.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENTS

Figure 1:
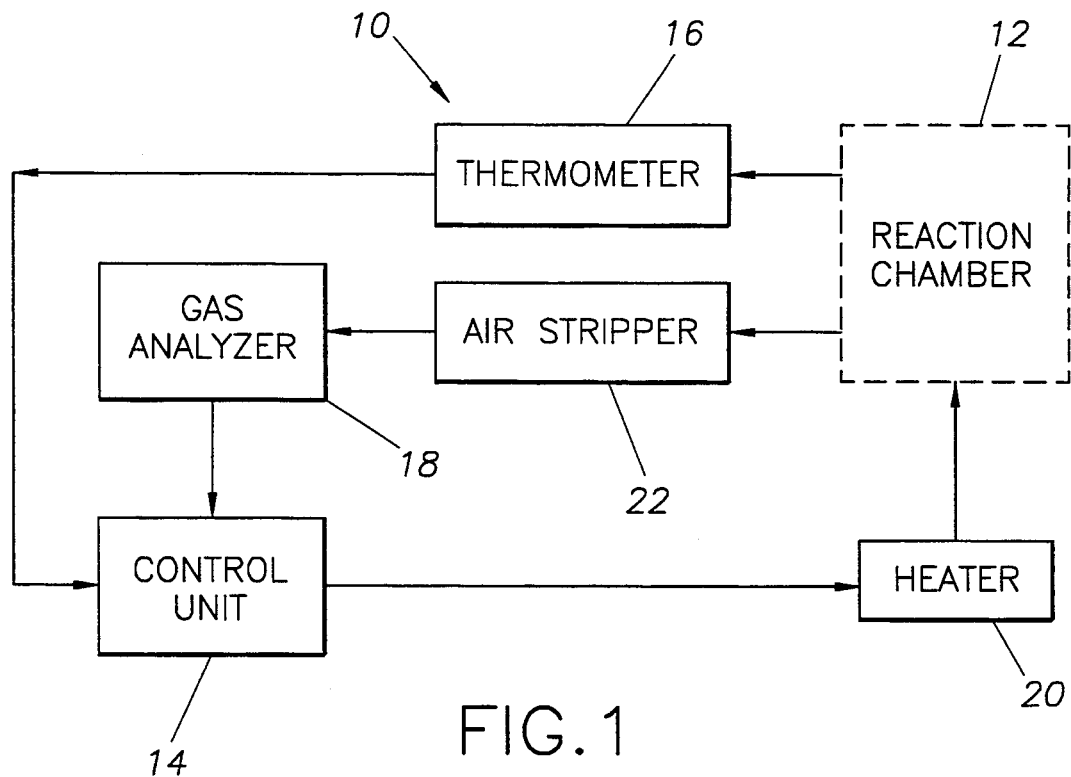
FIG. 1 is a component diagram of the single loop feedback control system of the present invention.

Referring initially to FIG. 1, the single loop feedback control system for an infectious waste treatment system is schematically shown and generally designated 10. Control system 10 is used to regulate the decontamination of waste in a reaction chamber 12 (phantom).

The primary element of the control system 10 is the control unit 14 which is preferably a microprocessor and a memory as is well known to those skilled in the art. Control unit 14 is in electrical communication with thermometer 16, gas analyzer 18, and heater 20. Control unit 14 regulates the heat output of heater 20 in response to the input parameters to unit 14 which are the $ClO_2$ concentration and the temperature of the liquid medium in reaction chamber 12. Disinfectant concentration data is provided to control unit 14 by means of a conventional air stripper 22 in fluid communication with chamber 12 and gas analyzer 18. Temperature data is provided to unit 14 from a conventional thermometer 16 which includes a temperature probe installed in reaction chamber 12.

Figure 2:
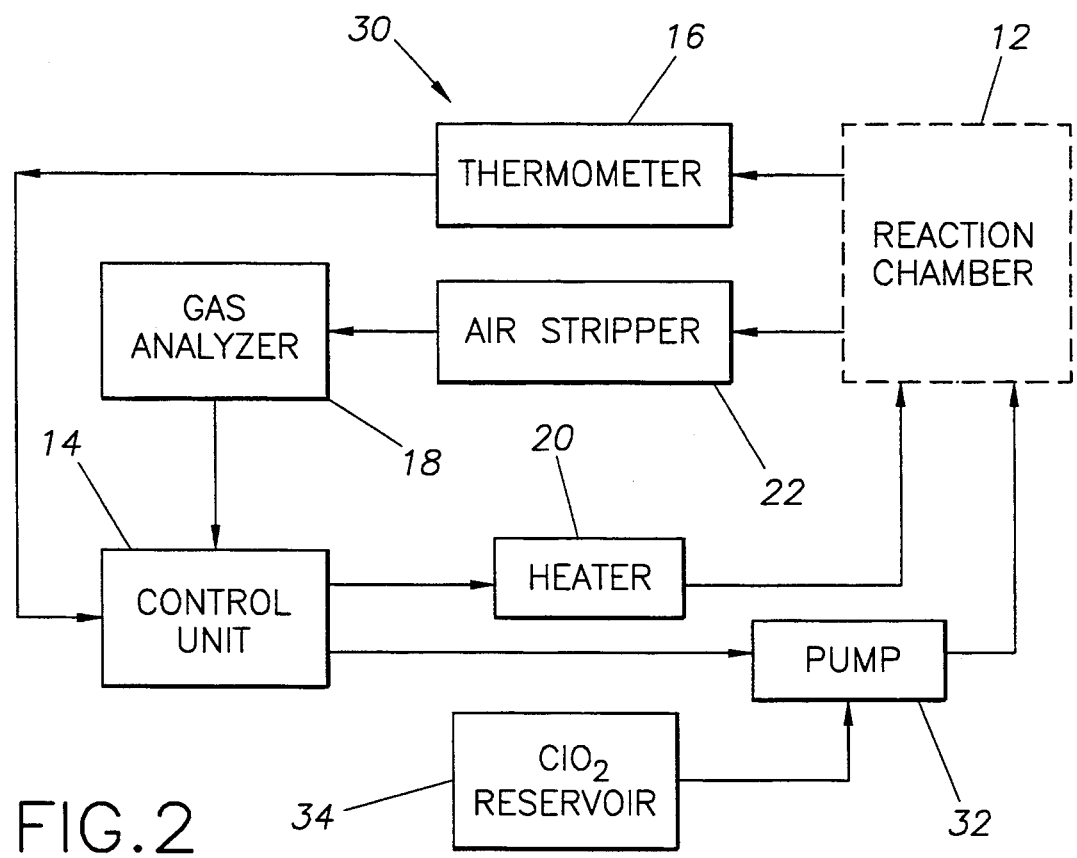
FIG. 2 is component diagram of the cascade loop feedback control system of the present invention.

Referring now to FIG. 2, the cascade loop feedback system of the present invention is schematically shown and designated 30. System 30 is substantially similar to system 10 and includes a control unit 14, thermometer 16, gas analyzer 18, heater 18, and air stripper 22 used in conjunction with reaction chamber 12 (phantom). Additionally, system 30 includes a pump 32 in electrical communication with control unit 14. Pump 32 is also in fluid communication with reaction chamber 12 and a reservoir 34 containing additional disinfectant in solution. Pump 34 is operable by control unit 14 to move disinfectant from reservoir 34 to chamber 14.

Included with the control unit 14 is the capability to allow the operator to input data into the control unit. This capability preferably is a keypad and a visual display indicating the inputted data. As those skilled in the art will appreciate a variety of other means could likewise be used including, but not limited to a keyboard, card reader, or down loading from a remote computer. The visual display of the preferred system can be an LED readout or other display such as a CRT screen or any other display means known in the art. The display preferably indicates not only the data inputted by the operator, but also the actual chamber temperature and disinfectant concentration.

As those skilled in the art will appreciate, the control unit 14 can include a single microprocessor if control functions are to be performed sequentially. Alternatively, if the control functions are to be performed simultaneously a plurality of microprocessors can be included in the control unit 14.

OPERATION

With cross-reference to the drawings, operation of systems 10 and 30 in a continuous mode may be seen. Systems 10 and 30 are particularly suited to the treatment of infectious wastes generated by hospitals and other medical facilities. Such wastes are primarily solid wastes consisting of plastic, paper, fabric, glass, and metal and embody a broad range of medical items including syringes, bottles, tubes, dressings, and the like. "Waste treatment" as the term is used herein constitutes fragmenting of the waste to a relatively small granular particle size and disinfecting the waste to render it substantially innocuous and suitable for ordinary landfilling.

The infectious waste is preferably shredded, granulated and mixed with an initial quantity of disinfectant prior to being decontaminated in a reaction chamber. As will be appreciated by those skilled in the art and discussed in greater detail below, system 30 can also be used to regulate decontamination of waste not mixed with disinfectant prior to entering the reaction chamber.

Process control for the decontamination process is provided by control unit 14. The decontamination level, i.e., level of kill, attainable in the decontamination process is a function of several interrelated operating parameters including disinfectant concentration and temperature.

Accordingly, process control can be effected by selecting a desired level of kill, i.e., rate of kill, and adjusting the disinfectant concentration and disinfectant solution temperature as a function of the operating parameters to meet the preselected rate of kill. For example, a rate of kill of 6 decades ($10^6$ organisms/ml) is achieved within about three minutes for typical infectious medical waste using a chlorine dioxide solution at a concentration of 30 ppm and a temperature of 50° C.

When using single loop control system 10, the process is controlled by adjusting only temperature while monitoring variations in the disinfectant concentration as a baseline for temperature adjustment. Temperature is selected as the independent variable and disinfectant concentration as the dependent variable for the practical reason that the ability to independently adjust disinfectant concentration is somewhat limited when a fixed amount of disinfectant is employed. On the other hand, it is relatively easy to adjust solution temperature via heater 20.

Figure 3:
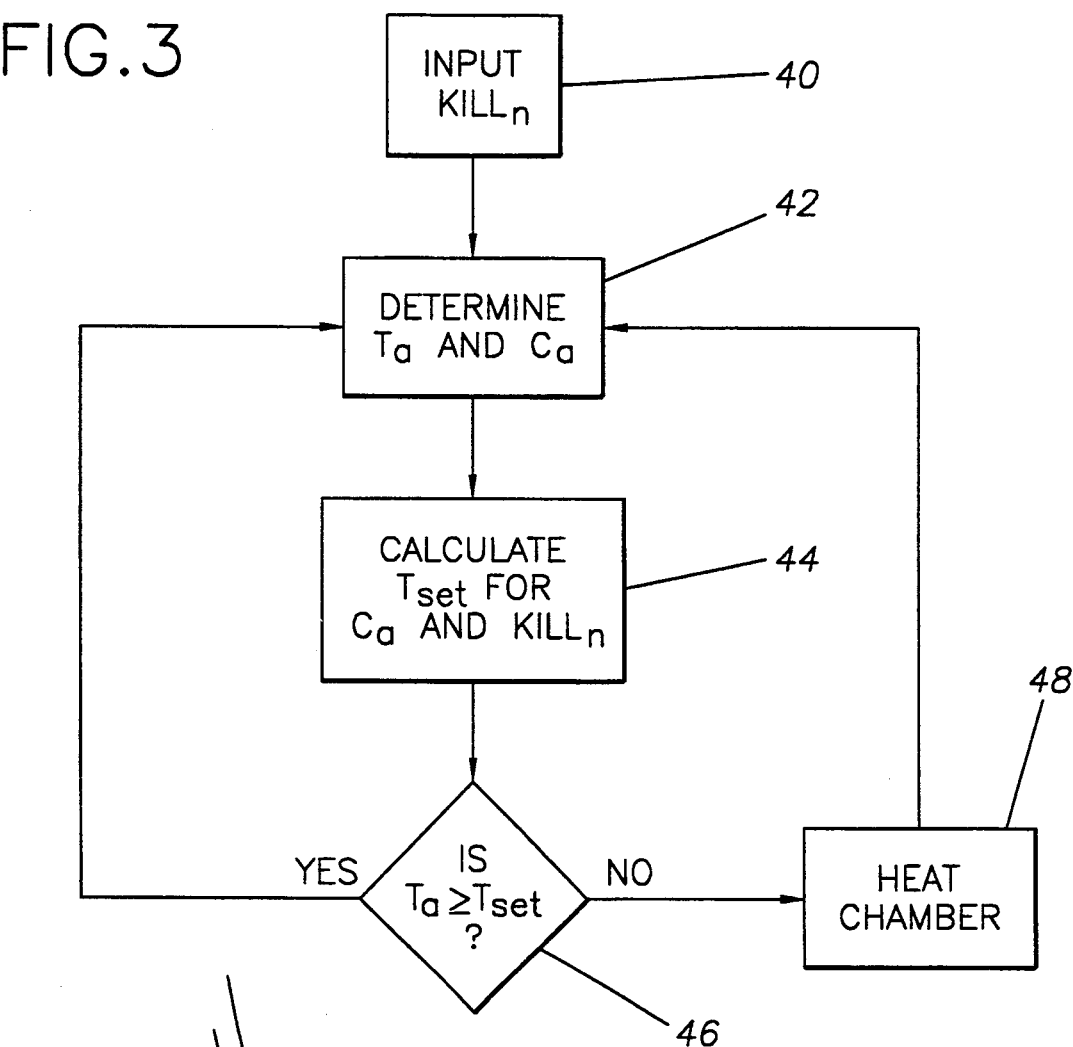
FIG. 3 is a logic flow chart of the operation of the single loop feedback control system of the present invention.

Referring now to FIG. 3, the logic flow chart for the single loop feedback control system 10 is shown. To begin, the rate of kill desired, namely $kill_n$, must be specified as is indicated in step 40. In the preferred embodiment, the control system allows the operator to input a desired $kill_n$. Alternatively, the control system can include a preset value for the rate of kill which may be overridden by the operator.

The next step in the control process, step 42, is the determination of the actual temperature ($T_a$) and disinfectant concentration ($C_a$) in the reaction chamber. As is well known in the art, the control unit can be programmed to periodically receive and store inputs from the thermometer 16 and the gas analyzer 18. Once this data is stored, it can be used for later calculations, as required.

Figure 5:
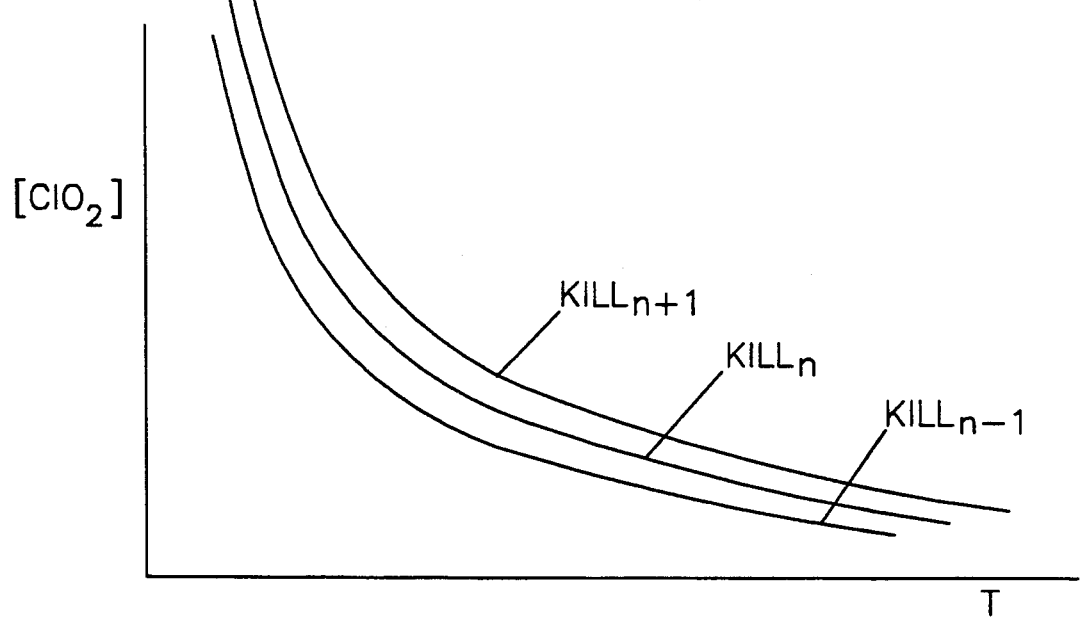
FIG. 5 is a generalized curve for the functional relation between reaction chamber temperature and disinfectant concentration for several rates of kill.

Step 44 is the use by the control unit of the actual disinfectant concentration, $C_a$, and the desired $kill_n$ to determine a temperature set point, $T_{set}$. Control system 10 recognizes the functional relationship between solution temperature and concentration of the disinfectant, chlorine dioxide, at a given rate of kill, $kill_n$. The relationship is represented by the equation:

$$[ClO_2] = a_n e^{-k_n T} \qquad (1)$$

wherein $[ClO_2]$ = chlorine dioxide concentration,
T = temperature, and
$a_n$, $k_n$ = empirically determined model constants for $kill_n$. FIG. 5 generally depicts the shape of the curve for equation (1). Each point on the curve defines values of $[ClO_2]$ and T at which $kill_n$ can be achieved. Accordingly, process control is more specifically implemented by preselecting the rate of kill, empirically determining the model constants at the rate of kill to define a curve, and adjusting the actual values of $[ClO_2]$ and T to lie on or above the rate of kill curve. Also shown in FIG. 5 are curves corresponding to a higher rate of kill, $kill_{n+1}$ as well as a lower rate, $kill_{n-1}$. As is to be expected, increased rates of kill require either increased temperature or higher disinfectant concentrations, or both.

As those skilled in the art will recognize, empirically determined model constants, once determined, are preferably stored in the memory of the control unit for later use. Knowing $C_a$, equation (1) can be solved for T and the minimum temperature (Tset) required to achieve $kill_n$ can be determined mathematically.

Returning to FIG. 3, once $T_{set}$ is determined as described above, the control unit 14 performs the comparison step 46. This comparison checks to see if $T_a$ is greater or equal to $T_{set}$. If not, then the control unit 14 operates heater 20 to increase $T_a$, step 48.

Control unit 14 can be programmed to operate heater 20 for a predetermined length of time, but preferably the duration of heater operation is proportional to the difference between $T_{set}$ and $T_a$. As those skilled in the art will appreciate, this allows the corrective change in $T_a$ to occur with less iterations of the control loop thereby improving the reaction speed of the control system. Heating the chamber can be accomplished in a number of ways including heating the chamber space itself. Preferably an immersion heater would be used to heat the disinfectant collecting in the reaction chamber and as the disinfectant is circulated, heat is passed to the waste. With this system, the temperature probe of thermometer 16 is also preferably located in the collected disinfectant and the chamber temperature is determined by measuring the temperature of the disinfectant being circulated.

If $T_a$ is greater than or equal to $T_{set}$, then the control unit returns to step 42, updates its stored values for $C_a$ and $T_a$ and repeats steps 44 and 46. Likewise, if the heater 20 has been operated the control unit 14 returns to step 42 and the cycle is repeated for another iteration.

Figure 4:
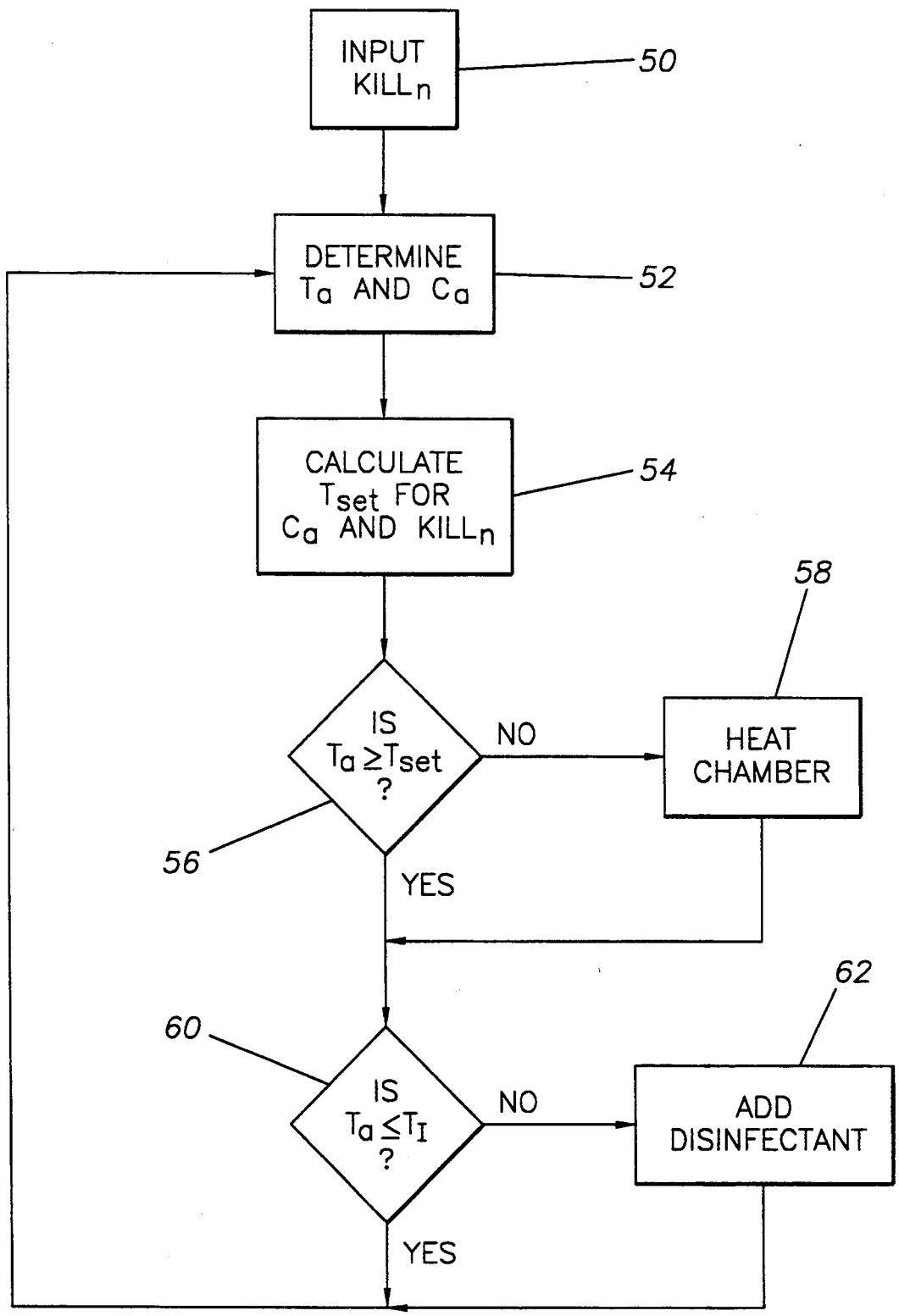
FIG. 4 is a logic flow chart of the operation of the cascade loop feedback control system of the present invention.

Referring now to FIG. 4, the logic flow chart for the cascade loop feedback control system 30 is shown. As is shown, logic steps 50, 52, 54, 56 and 58 are substantially the same as single loop system steps 40, 42, 44, 46 and 48. The only difference is that after operation of the heater, step 58 or determining that $T_a$ is greater than or equal to Tset, step 56, a second comparison is performed instead of repeating the first loop.

This second comparison, step 60, has the control unit 14 comparing $T_a$ to an ideal operating temperature $T_I$. Preferably $T_I$ will be predetermined and stored by the control unit 14. Alternatively, control unit 14 could be programmed to allow the operator to input $T_I$. In any event, if the comparison between $T_a$ and $T_I$ indicates Ta is greater than $T_I$, then the control unit operates pump 32 to add disinfectant to the reaction chamber, step 62. After the second control loop is complete, the process is repeated starting with the control unit updating $T_a$ and $C_a$. In step 62, the pump 32 preferably adds disinfectant at a rate proportional to the difference between $T_a$ and $T_I$. It is to be appreciated that control unit 14 could likewise be programmed to add a set amount of disinfectant instead, but the performance of the control system would be degraded.

As those in the art will appreciate, some fluid leaves the system with the decontaminated waste. To compensate for this fluid loss, additional unheated water is added to the reaction chamber. The temperature of the water being added is generally below the temperature of the fluid in the reaction chamber. Thus, the lowered heating requirement which is the result of the additional disinfectant, combined with the addition of unheated water lowers the temperature of the fluid in the reaction chamber.

The logic flow chart shown in FIG. 4 is for a system including a single microprocessor in the control unit 14. The speed of modern microprocessors makes the sequential processing of the respective control loops nearly simultaneously. If true simultaneous processing is desired, separate microprocessors could be used to process the two control loops.

Figure 6:
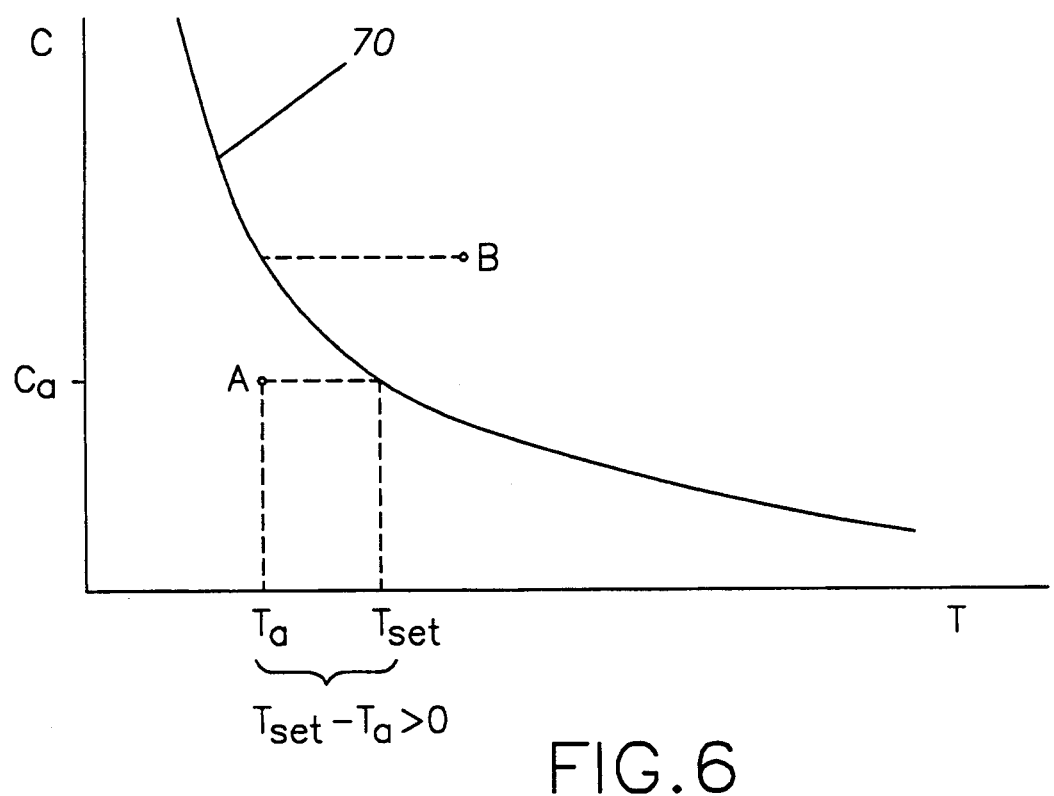
FIG. 6 is a generalized curve for the functional relation between reaction chamber temperature and disinfectant concentration showing operation of the single loop system.

In order to fully appreciate the operation of control systems 10 and 30, specific examples of their operation can be shown. Referring now to FIG. 6, the specific examples of the operation of control system will be shown.

Curve 70 is shown for the desired rate of kill. If the actual temperature and disinfectant concentration correspond to point A, control unit 14 would calculate $T_{set}$, and the comparison would indicate $T_a$ is less than $T_{set}$. The calculation and comparison are graphically depicted in FIG. 6. To correct the low temperature, the heater 20 would be operated to increase the chamber temperature. On the other hand, if the temperature and concentration correspond to point B, then $T_{set}$ would be less than $T_a$ and no additional heat would be required.

Figure 7:
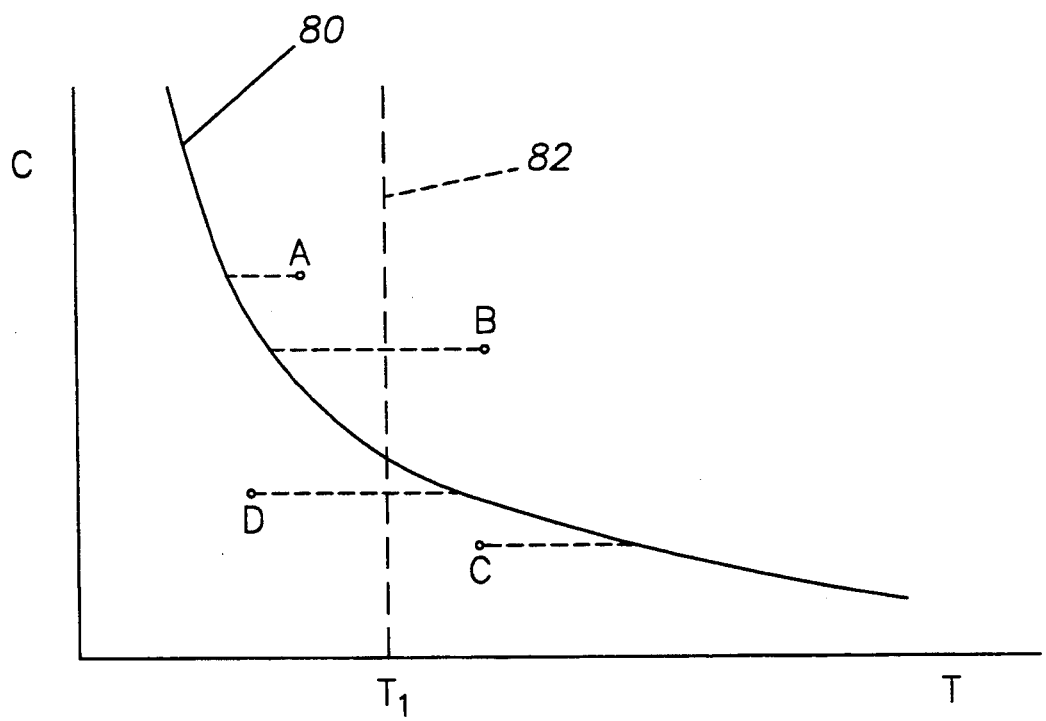
FIG. 7 is a generalized curve for the functional relation between reaction chamber temperature and disinfectant concentration showing operation of the cascade loop system.

Referring now to FIG. 7, possible examples of operation are shown for cascade system 30. Curve 80 is shown for the desired rate of kill. Additionally, $T_I$ is designated by line 82. Four possible temperature-concentration combinations are shown and designated points A, B, C and D.

Point A represents the situation where $T_a$ is greater than $T_{set}$, but less than $T_I$. Here, the control unit 14 will neither heat the reaction chamber, nor add disinfectant.

Point B represents the situation where $T_a$ is greater than $T_{set}$ and is greater than $T_I$. Here control unit 14 would operate the disinfectant pumps which, as discussed above, tends to cool the fluid in the chamber.

Point C represents the situation where $T_a$ is less than $T_{set}$, but is greater than $T_I$. Here, control unit 14 would operate both the pump 32 and the heater 20.

Point D represents the situation where $T_a$ is less than $T_{set}$, and is less than $T_I$. Here, control unit 14 would operate only the heater 20.

In the preferred embodiment, disinfectant is added to the chamber with the waste, and the systems are used to monitor and maintain sufficient disinfectant concentrations and temperatures to decontaminate the waste at or above the desired rate of kill. As those skilled in the art will appreciate, the control system 30 could be used to supply all of the disinfectant required as long as a sufficient reservoir 34 is supplied including sufficient amounts of fresh disinfectant contained therein.

While the particular Control System for Medical Waste Disposal as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for regulating decontamination of waste in a reaction chamber to, maintain a specified rate of kill as the waste pass through the reaction chamber, said reaction chamber having a chamber temperature and a liquid disinfectant concentration, said device comprising:

means for measuring said chamber temperature of said reaction chamber;

a means for determining said disinfectant concentration of said reaction chamber;

a means for heating said reaction chamber; and a control unit connected to said measuring means, said determining means and said heating means, said control unit calculating a set point temperature as a function of said specified rate of kill and said disinfectant concentration and maintaining said specified rate of kill by monitoring said chamber temperature and said chamber disinfectant concentration and selectively operating said heating means to heat said reaction chamber when said heating means to below said set point temperature.

2. The device as recited in claim 1 wherein said control unit calculates a set point temperature as a function of said specified rate of kill and said disinfectant concentration, said control unit maintaining said chamber temperature at or above said set point temperature by operating said heating means to heat said chamber when said chamber temperature is below said set point temperature.

3. The device as recited in claim 1 further comprising a pump connected to and control unit, said pump being in fluid communication with said chamber and a reservoir containing disinfectant, said pump moving disinfectant for said reservoir to said chamber when said control unit determines said chamber temperature exceeds a predetermined ideal temperature $T_I$.

4. The device as recited in claim 1 wherein said means for measuring temperature of said reaction probe in said reaction comprises a thermometer having a temperature probe in said reaction chamber, said thermometer being electrically connected to said control unit.

5. The device as recited in claim 1 wherein said means for determining disinfectant concentration of said reaction chamber comprises a gas analyzer electrically connected to said control unit.

6. The device as recited in claim 5 wherein said means for determining disinfectant concentration of said reaction chamber further comprises an air stripper in fluid communication with said reaction chamber and said gas analyzer, said stripper selectively removing gas samples from said chamber and providing said gas samples to said gas analyzer.

7. The device as recited in claim 2 wherein said control unit comprises a CPU and a memory connected to said CPU.

8. The device as recited in claim 7 wherein said control unit further comprises a keypad for entry of said specified rate of kill by an operator, said key pad being electrically connected to said CPU.

9. The device as recited in claim 8 wherein said control unit further comprises a visual display indicating said specified rate of kill entered by said operator, said visual display being electrically connected to said CPU.

10. The device as recited in claim 9 wherein said visual display further indicates said chamber temperature and said chamber disinfectant concentration.

11. A device for regulating decontamination of waste in a reaction chamber to maintain a specified rate of kill as the waste passes through the reaction chamber, said reaction chamber having a chamber temperature and a liquid disinfectant concentration, said device comprising:
  a means for inputting said specified rate of kill;
  a means for measuring said chamber temperature of said reaction chamber;
  a means for determining said disinfectant concentration of said reaction chamber;
  a means for heating said reaction chamber;
  a means for adding disinfectant to said reaction chamber; and
  a control unit connected to said measuring means, said determining means, said heating means and said adding means, said control unit calculation a set point temperature as a function of said rate of kill and said chamber disinfectant concentration and maintaining said specified rate of kill by monitoring said chamber temperature and said chamber disinfectant concentration and selectively operating said adding means when said chamber temperature exceeds a predetermined ideal temperature $T_I$ and selectively operating said heating means when said chamber temperature is below said set point temperature in order to maintain said specified rate of kill.

12. The device as recited in claim 11 wherein said control unit calculates a set point temperature as a function of said rate of kill and chamber disinfectant concentration.

13. The device as recited in claim 11 wherein said means for measuring temperature of said reaction chamber comprises a thermometer having a temperature probe in said reaction chamber, said thermometer being electrically connected to said control unit.

14. The device as recited in claim 11 wherein said means for adding disinfectant to said reaction chamber comprises a pump in fluid communication with said reaction chamber and a reservoir containing said disinfectant from said reservoir to said pump selectively moving disinfectant from said reservoir to said chamber.

15. The device as recited in claim 14 wherein said control unit selectively operates said heating means when said chamber temperature is below said setpoint temperature and selectively operates said adding means when said chamber temperature is above said ideal temperature.

16. The device as recited in claim 11 wherein said means for determining disinfectant concentration of said reaction chamber comprises a gas analyzer electrically connected to said control unit.

17. The device as recited in claim 16 wherein said means for determining disinfectant concentration of said reaction chamber further comprises an air stripper in fluid communication with said reaction chamber and said gas analyzer, said air stripper selectively removing air samples from said chamber and providing said air samples to said gas analyzer.

18. The device as recited in claim 11 wherein said control unit comprises a CPU and a memory connected to said CPU.

19. The device as recited in claim 18 wherein said inputting means comprises a keypad for entry of said specified rate of kill by an operator, said key pad being electrically connected to said CPU.

20. The device as recited in claim 19 wherein said control unit further comprises a visual display indicating said specified rate of kill entered by said operator, said visual display being electrically connected to said CPU.

21. The device as recited in claim 20 wherein said visual display further indicates said chamber temperature and said chamber disinfectant concentration.

22. A method for regulating decontamination of waste in a reaction chamber to maintain a specified rate of kill as the waste passed through the reaction chamber, said reaction chamber having a chamber temperature and a disinfectant concentration, said method comprising the steps of:
  monitoring said chamber temperature using a thermometer having an electrical output;
  monitoring said disinfectant concentration using as gas analyzer having an electrical output;
  calculating a set point temperature as a function of said rate of kill and said disinfectant concentration using a control unit connected to said analyzer, said control unit having as inputs the electrical outputs of said thermometer and said gas analyzer; and
  maintaining said rate of kill by heating said reaction chamber when said chamber temperature is below said calculated set point temperature.

23. The method as recited in claim 22 further comprising the step of adding disinfectant to said reaction chamber when said chamber is above an predetermined ideal temperature $T_I$.

24. The method as recited in clam 23 wherein said adding disinfectant step comprises:
  providing a reservoir containing said disinfectant and a pump in fluid communication with said reservoir and said chamber; and
  operating said pump to move said disinfectant from said reservoir to said chamber.

25. A method for regulating decontamination of waste in a reaction chamber to maintain a specified rate of kill as the waste passes through the reaction chamber, said reaction chamber having a chamber temperature and a disinfectant concentration, said method comprising the steps of:

a. monitoring said chamber temperature using a thermometer having an electrical output;
b. monitoring said disinfectant concentration using a concentration analyzer having an electrical output;
c. calculating a set point temperature, as a function of said rate of kill and said disinfectant concentration, using a control unit connected to said thermometer and said gas analyzer, said control unit having as inputs the electrical outputs of said thermometer and said gas analyzer;
d. maintaining said rate of kill by heating said reaction chamber when said chamber temperature is below said calculated set point temperature; and
e. repeating steps c. and d. at predetermined intervals during the decontamination process.

26. The method as recited in claim 25 wherein said maintaining step comprises the sub-step of adding disinfectant to said reaction chamber when said chamber is above an predetermined ideal temperature $T_I$.